United States Patent [19]

Ezekiel et al.

[11] 4,198,031
[45] Apr. 15, 1980

[54] AUTOMATIC AIR DEFLATION REGULATOR FOR USE IN AN INSTRUMENT FOR MEASURING BLOOD PRESSURE

[75] Inventors: Frederick D. Ezekiel, Lexington; Sol Aisenberg, Natick, both of Mass.

[73] Assignee: Gulf & Western Industries, Inc., New York, N.Y.

[21] Appl. No.: 896,968

[22] Filed: Apr. 17, 1978

[51] Int. Cl.² ............................................. F16K 24/00
[52] U.S. Cl. .................................. 251/117; 137/844; 138/45; 128/685
[58] Field of Search ....................... 251/117; 137/844; 138/45; 128/2.05 G

[56] References Cited

U.S. PATENT DOCUMENTS

| | | | |
|---|---|---|---|
| 2,389,134 | 11/1945 | Brown | 138/45 |
| 2,629,393 | 2/1953 | Langdon | 137/844 X |
| 2,941,544 | 6/1960 | Peras | 138/45 X |
| 3,077,903 | 2/1963 | Honsinger | 138/45 |
| 3,187,947 | 6/1965 | Ellis | 138/45 X |
| 3,504,663 | 4/1970 | Edwards | 128/2.05 G |
| 4,072,171 | 2/1978 | Nakazawa | 128/2.05 G |

FOREIGN PATENT DOCUMENTS 393956  11/1965  Switzerland .............................. 137/844

*Primary Examiner*—Arnold Rosenthal
*Attorney, Agent, or Firm*—Gregory J. Battersby; Kenneth E. Merklen; Thomas E. Harrison, Jr.

[57] ABSTRACT

An automatic air deflation valve is provided for use with a sphygmomanometer type blood pressure measuring instrument. The valve comprises a housing having an air flow channel extending through the longitudinal extent thereof and at least one air deflation port extending outwardly from said channel. The port includes a deformable diaphragm supported only on its outer edges and having a central aperture extending through the thickness thereof. The diaphragm is adapted to deform in accordance with the air pressure applied against it from said channel to automatically adjust the size and shape of said aperture, thus producing a constant air deflation rate therethrough.

13 Claims, 8 Drawing Figures

AUTOMATIC AIR DEFLATION REGULATOR FOR USE IN AN INSTRUMENT FOR MEASURING BLOOD PRESSURE

BACKGROUND OF THE INVENTION

The present invention relates generally to an automatic air deflation regulator for use in a blood pressure measuring instrument and, more particularly, to such a regulator which includes a deformable diaphragm having an aperture adapted to increase and decrease in size as a function of the air pressure applied against the diaphragm.

In conventional sphygmomanometer blood pressure instruments, an inflatable cuff is affixed around the extremity of an individual whose blood pressure is to be measured. The cuff is inflated sufficiently to constrict the flow of arterial blood passing through the extremity and then the pressure in the cuff is decreased at a controlled and known rate of deflation until such time as the Korotkoff sound is first heard through a stethoscope or other monitoring device. Deflation continues until the Korotkoff sound ceases. The pressure at the commencement of the sound is noted and recorded as the systolic pressure and at the time it stops as the diastolic pressure.

As it is of utmost importance to maintain a constant rate of deflation, so that the pressure decreases linearly with time, deflation in such instruments is normally controlled by a valve through which air is released at a constant rate. As can readily be appreciated, when the valve has a fixed orifice, air will escape at higher pressures much more rapidly than at lower pressures and this results in a decreasing rate of deflation. This can and does result in inaccurate blood pressure readings. To compensate for this, most blood pressure measuring instruments rely on a manually adjustable release valve which permits constant adjustment of the size of the orifice to accommodate for a decrease in air pressure to maintain this fixed or constant deflation rate. Such manually adjustable valves, however, require operation by physicians, nurses or other trained technicians since a degree of skill is required in order to properly adjust the valve to achieve a constant deflation rate.

With the increased public realization of the importance of monitoring one's blood pressure, there has been a growing demand for such instruments which can be used by an individual in measuring his or her own blood pressure. Since most individuals are not trained and therefore may not possess the skill required to properly adjust the control valves to achieve the constant deflation required to insure accurate and reproduceable readings, two approaches have been taken. Certain manufacturers have provided instruments with a fixed orifice valve. The disadvantages of such a valve have been discussed—they do not provide accurate readings because of their inherent non-constant deflation rate. Other manufacturers have tried semi-automatic valves which attempt to compensate for the decreasing air pressure in order to provide a constant deflation rate. An example of one such valve is described in U.S. Pat. No. 3,504,663 which issued to W. C. Edwards on Apr. 7, 1970. Semi-automatic valves of this type, however, still require a certain amount of adjustment to effect constant deflation and, if improperly adjusted, will not achieve the requisite constant deflation rate. Moreover, such valves are easily clogged by impurities in the air passing through them.

Against the foregoing background, it is a primary objective of the present invention to provide an air deflation regulator or valve for use in an instrument for measuring blood pressure which is capable of providing a constant rate of deflation.

It is still another object of the present invention to provide such an air deflation valve which does not require manual adjustment to compensate for air pressure changes.

It is still another object of the present invention to provide such an air deflation valve which can be easily manufactured.

SUMMARY OF THE PRESENT INVENTION

To the accomplishments of the foregoing objects and advantages, the present invention briefly comprises an automatic air deflation valve which can be used with a sphygmomanometer. The valve comprises a housing having an air flow channel extending through the longitudinal extent thereof and at least one air deflation port extending outwardly from said channel. The port includes a deformable diaphragm supported on only its outer edges and having a central aperture extending through the thickness thereof. The diaphragm is adapted to deform in accordance with the fluid pressure applied against it from said channel in order to automatically adjust the size and shape of said aperture to produce a constant rate of air pressure deflation therethrough.

BRIEF DESCRIPTION OF THE DRAWINGS

The foregoing and still other objects and advantages of the present invention will be made apparent from the following detailed explanation of the preferred embodiments of the invention in connection with the accompanying drawings, wherein.

DESCRIPTION OF THE PREFERRED EMBODIMENTS

Figure 1:
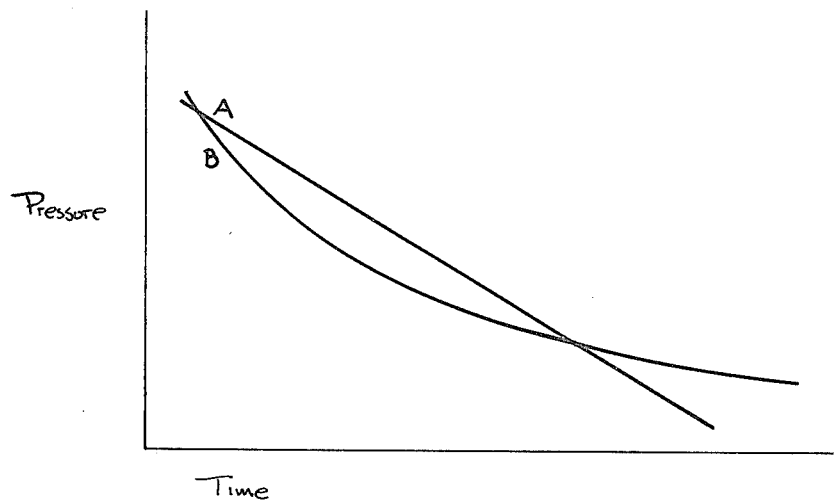
FIG. 1 is a graph plotting air pressure through both a fixed orifice and through the valve of the present invention as a function of time.

The objective of the present invention is to provide a valve which can automatically produce a linear air pressure deflation as shown in curve A of FIG. 1 which plots air pressure as a function of time. In the measurement of human blood pressure, the American Heart Association has recommended an air deflation rate of between about 2 and about 3 mm mercury/- second. Curve B of FIG. 1 illustrates the rate of air deflation through a fixed orifice valve which, as shown in this curve, produces a rapid rate of deflation at higher pressures and a greatly reduced or flat rate of air deflation through the valve at lower pressures.

Figure 2:
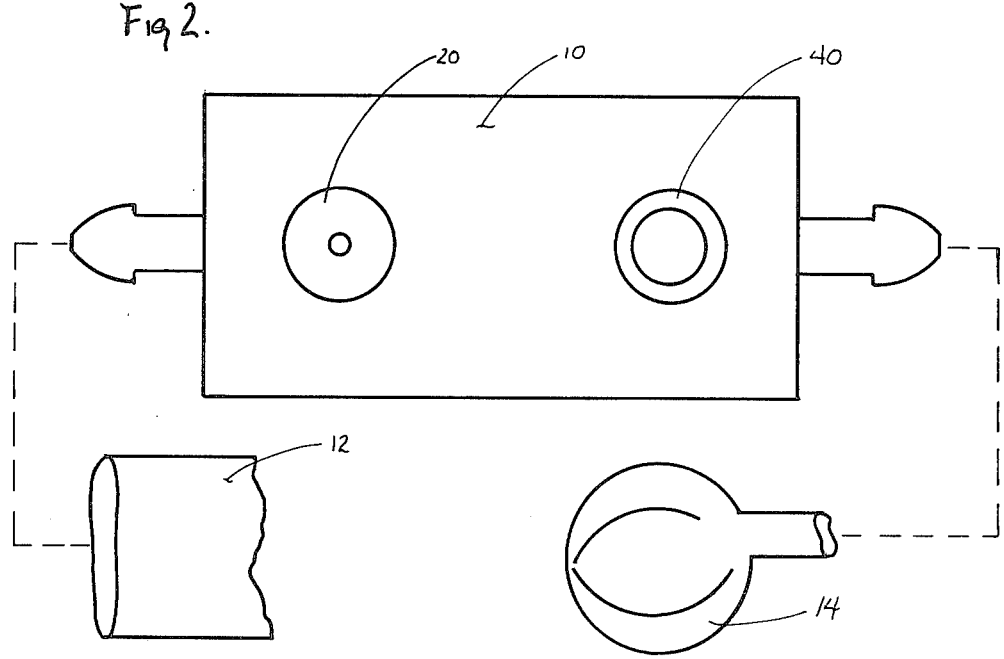
FIG. 2 is a top schematic view showing the air valve of the present invention relative to a conventional blood pressure measurement system.

The air deflation regulator valve of the present invention, referred to generally by reference numeral 10, is shown in FIG. 2. Air deflation regulator valve 10 is connected by conventional rubber or plastic tubing between a pressure cuff 12 and a squeeze-bulb or bladder 14 forming an otherwise standard or conventional sphygmomanometer-type blood pressure measuring instrument. Air is introduced from the bladder 14 through the regulator valve 10 to the pressure cuff 12 which is adapted to be placed around the extremity of a person whose blood pressure is being measured. Air pressure is increased to a level above the point at which the arterial blood flow is stopped and then by introducing no additional air, deflation of the air pressure within cuff 12 commences through the deflation port 20 of the regulator valve 10. Regulator valve 10 may also include quick release port 40 for rapid depressurization when required.

Figure 3:
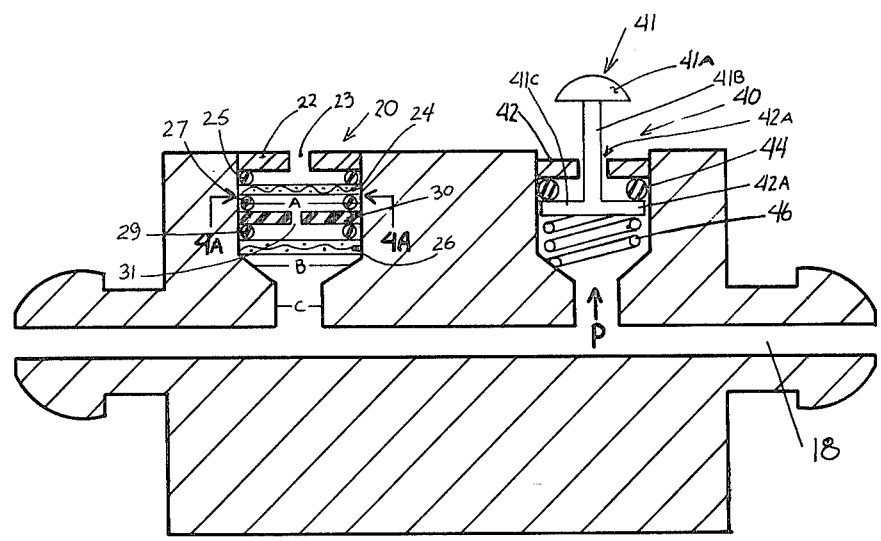
FIG. 3 is a horizontal cross-sectional view of the air regulator valve of the present invention in an unpressurized state.

As shown schematically in FIG. 2 and in greater detail in sectional view FIG. 3, air deflation regulator valve 10 includes a central fluid or air flow channel 18 through which air is transmitted from the bladder 14 to the cuff 12. Deflation port 20 and quick release port 40 are open at their inlet portions to the channel 18.

Deflation port 20 is substantially closed at the top by an outer ring 22 with a central fixed orifice 23, preferably circular or round in shape. A pair of circular screens 24 and 26 are provided both above and below a deformable diaphragm 30 having a central aperture 31 extending through the thickness thereof. This sandwich structure of screens 24 and 26 and diaphragm 30 is maintained in place by three O-rings 25, 27 and 29 located between outer ring 22 and upper screen 24; between upper screen 24 and the diaphragm 30; and between the diaphragm 30 and the lower screen 26, respectively.

Deflation port 20 has a substantially uniform inner diameter A in which the sandwich structure is contained and preferably tapers in a neck portion B to an inlet C at the channel 18.

Outer ring 22 which may be fabricated from either a plastic material such as, for example, lucite or metal such as, for example, stainless steel, may be retained in deflation port 20 by a pressure fit as shown, for example, in FIG. 3, or by other suitable affixation means including, for example, by threadably engaging the outer ring 22 with the port 20 or by the use of an adhesive such as, for example, an epoxy resin. Central aperture 23 of outer ring 22 is preferably round in shape although it may assume virtually any shape and size since it is intended to permit the passage of air through central aperture 23 yet minimize the possibility of a contaminant entering and clogging the aperture of the diaphragm 30. Accordingly, aperture 23 should only be of sufficient size and shape to permit the passage of air without creating undue back pressure.

Upper and lower screens 24 and 26 are provided to further screen out any impurities or contaminants in the air passing through the deflation port 20 in order to prevent the aperture 31 of the diaphragm 30 from clogging. Screens 24 and 26, which are circular in shape, may be fabricated from either a metal or a plastic material and the size of the mesh should only be sufficient to permit the passage of air through it without creating undue back pressure.

The diaphragm 30 includes a central aperture 31 which is preferably rectangular, square or circular in shape and must be sufficiently deformable or elastic to conform to changes in air pressure applied against it. In order to achieve this degree of deformability, diaphragm 30 is fabricated from a ductile and flexible thermoplastic or thermoset material such as, for example, a silicone rubber, a pure gum or a polyurethane material with a catalyst, preferably an organo tin complex catalyst, such as, for example, the organo tin complex catalyst marketed by Emerson and Cuming, Inc. of Canton, Mass., under the trademark Catalyst 50. The diaphragm 30 should be made from a material which does not deform with time and further should be one which will volume-harden rather than surface-cure. Silicone rubber is preferred since it is the most stable with respect to age, pressure and temperature. A most preferred material for fabricating the diaphragm 30 is an RTV silicone rubber, such as the RTV silicone rubber marketed by Emerson & Cuming, Inc. under the trademark Eccosil. It has been found that if the hardness of diaphragm 30 is between about 50 and about 75 and most preferably between about 60 and about 72 Durometer Shore A, the diaphragm 30 will be sufficiently deformable to function effectively.

The thickness of the diaphragm should preferably be between about 0.020 and about 0.040 inches, however it may be thicker or thinner depending upon the operating air pressure and the size and shape of the central aperture 31.

Figure 4:
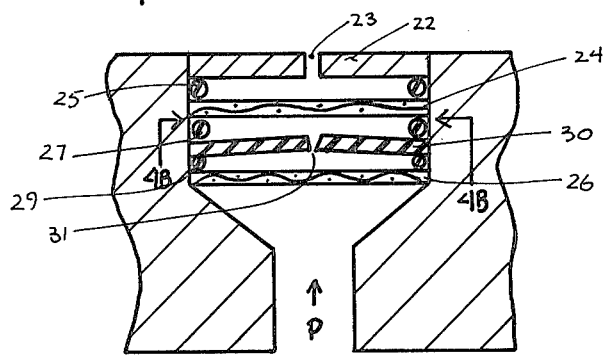
FIG. 4 is an enlarged partial sectional view of the air deflation port of the valve of FIG. 3 in a pressurized state.

Central aperture 31, which may be either rectangular, square, oval or round in shape, extends through the thickness of the diaphragm 30. A preferred configuration of central aperture 31, as shown in a sectional top view of FIG. 4A, is rectangular. When aperture 31 is rectangular, it is preferably between about 0.010 and about 0.050 inches long and between about 0.002 and about 0.010 inches wide. A most preferred shape and size of aperture 31 is a rectangular slit measuring about 0.003 inches wide and about 0.010 inches long. The actual size of the rectangular aperture 31 is determined by the thickness of the diaphragm 30 and its hardness.

Figure 4B:
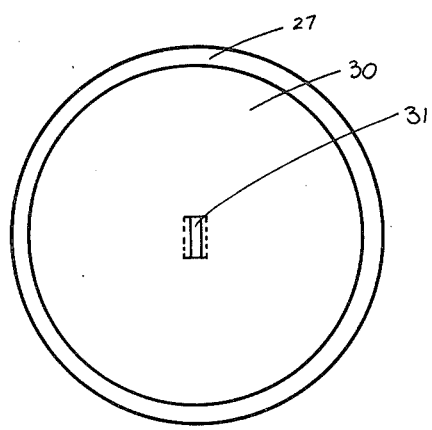
FIG. 4B is a sectional view taken along lines 4B—4B of FIG. 4.
Figure 4A:
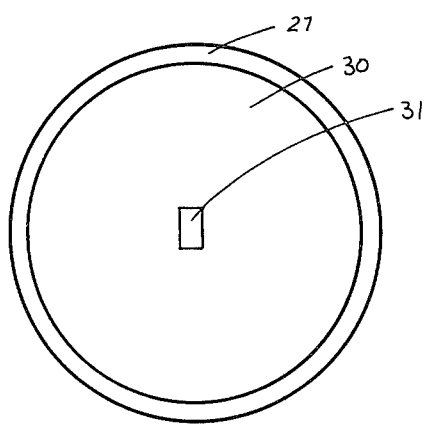
FIG. 4A is a sectional view taken along lines 4A—4A of FIG. 3.

As previously noted, central aperture 31 may also be round or circular in shape, as shown in FIG. 4B, and extend through the cross-sectional thickness of the diaphragm 30. When so shaped, the aperture should be between about 0.005 and about 0.010 inches in diameter with a preferred diameter being about 0.008 inches in diameter. Again, the actual dimension of the aperture 31 is a function of the thickness of the diaphragm 30 and its hardness.

The significance of providing a flexible, deformable diaphragm 30 with a central aperture 31 of the above-stated sizes and shapes is that when it is so placed in deflation port 20 supported only on its outer edge by O-rings 27 and 29 the size of the aperture 31 will vary depending upon the air pressure applied against it from channel 18. FIG. 3 illustrates the diaphragm 30 in an unpressurized state wherein the diaphragm is maintained in an undeformed state, generally perpendicular to the side walls of the uniform diametered portion A of the port 20. In an unpressurized state, central aperture 31 has a substantially uniform diameter or width throughout its entire horizontal extent through the thickness of the diaphragm 30.

In a pressurized state, however, such as, for example, when the cuff is being deflated during a blood pressure measurement, the air pressure P in channel 18 which is transmitted to the rear of diaphragm 30 causes diaphragm 30 to deform outwardly toward the outer ring 22 causing a restriction in central aperture 31 as shown in FIGS. 4 and 4B. The amount of restriction in central aperture 31 is dependent upon the amount of the air pressure P against it and the thickness and hardness of the diaphragm 30. At higher pressures, such as when measurement is first commenced, the size of the aperture 31 is the smallest due to the greater amount of deformation of the diaphragm 30, thus allowing the least amount of air to pass therethrough. As the air pressure P is reduced, the deformation of the diaphragm 30 is decreased thus increasing the size of the aperture 31 and permitting a greater amount of air to pass through the aperture 31. In this manner, the relatively constant deflation rate of curve A of FIG. 1 is achieved since, due to the deformation of the diaphragm 30, the aperture 31 increases and decreases in size as the air pressure P against it decreases and increases. This is in contrast to a fixed size orifice which produces, as illustrated in curve B of FIG. 1, a greater deflation rate at higher pressures and a lower deflation rate at lower pressures.

O-rings 25, 27 and 29 are conventional thermoplastic or thermoset O-rings and should be ductile. Like screens 24 and 26 and diaphragm 30, O-rings 25, 27 and 29 are preferably retained in place by a pressure fit to permit a free edge motion in order to provide a spring mounting of the diaphragm 30 to permit maximum deformation thereof.

An optional quick-release valve 40 is provided in quick release port 40A as shown in FIG. 3 for rapid depressurization of the cuff 12. Quick release valve 40 includes a plunger 41 which is spring restrained by spring 46 in the quick release port 40A. Plunger 41 includes a head portion 41A, a neck portion 41B and a base portion 41C. An O-ring 44 is provided between an outer ring 42 and plunger base 41C. Outer ring 42 includes a central aperture 42A in which the neck portion 41B of the plunger 41 is positioned. The diameter of the central aperture 42A is greater than the diameter of the neck portion 41B of the plunger 41. During operation of the blood pressure instrument, plunger 41 is loaded by spring 46 and the base portion 41C of the plunger 41 seals against the O-ring 44 thus preventing the release of air pressure P outwards from channel 18 through the quick release port 40. If rapid depressurization is required, the operator depresses plunger 41 and allows the pressure to be quickly released through the port 40 in the space between the neck portion 41B and the central aperture 42A.

Figure 6:
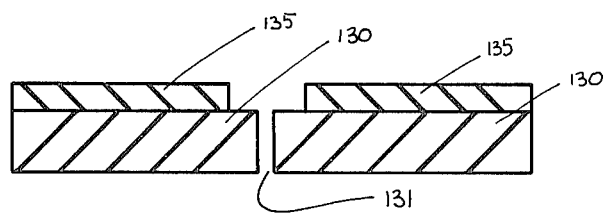
FIG. 6 is a sectional view taken along lines 6—6 of FIG. 5.
Figure 5:
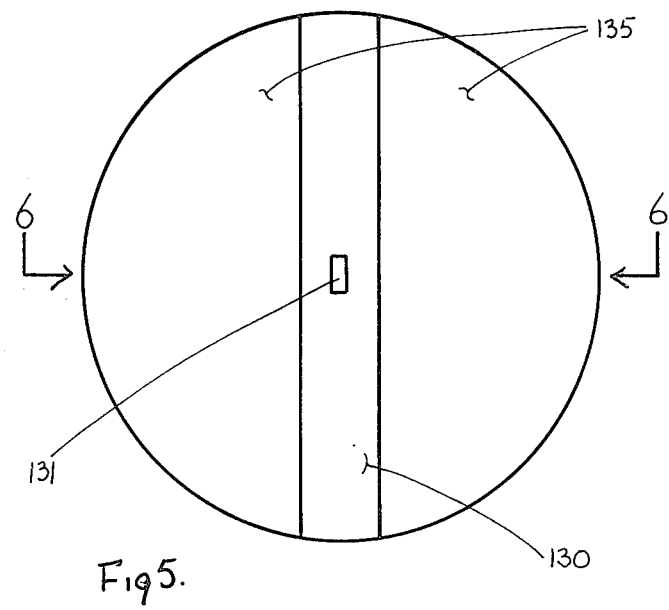
FIG. 5 is a top view of an alternative diaphragm of the present invention.

FIGS. 5 and 6 illustrate an alternative deformable diaphragm 130 which may be used in the embodiment of FIGS. 2-4. Deformable diaphragm 130 is identical to the earlier described diaphragm 30 of the other embodiment and includes a stiffener layer 135 of an epoxy or other like material on one surface thereof extending inwardly from the outer periphery thereof. The area of diaphragm 130 adjacent the aperture 131 is not reinforced or stiffened. In this manner, the outer edges of the diaphragm 130 are maintained relatively stiff while the area around the aperture 131 is unsupported and deformable. As such, increased air pressure P from channel 18 results in greater deformation of only the portion of the diaphragm 130 adjacent the aperture 131 thus making it more sensitive to slight air pressure variations.

Having thus described the invention with particular reference to the preferred forms thereof, it will be obvious that various changes and modifications may be made therein without departing from the spirit and scope of the invention as defined in the appended claims.

What is claimed is:

1. An automatic air pressure deflation regulator for use in a sphygmomanometer, said regulator comprising a housing having an air flow channel extending through the longitudinal extent thereof and at least one air deflation port extending outwardly from said channel, said at least one air deflation port including a floatably mounted, deformable diaphragm of substantially uniform thickness supported only on its outer edges by a pair of O-rings on either side of said diaphragm and having an aperture extending through the thickness thereof, said diaphragm adapted to axially deform along its entire longitudinal extent according to the air pressure applied against it from said channel in order to change the size and shape of said aperture as a function of the air pressure to produce a constant air deflation rate therethrough.

2. The valve of claim 1 wherein said deflation port includes at least one screen for filtering the air passing through said aperture.

3. The valve of claim 1 wherein said diaphragm is a silicone rubber material having a hardness between about 50 and about 75 Durometer Shore A.

4. The valve of claim 3 wherein said diaphragm is between about 0.020 and about 0.040 inches thick.

5. The valve of claim 1 wherein the shape of said aperture in an unpressurized state is rectangular.

6. The valve of claim 5 wherein said rectangular aperture is between about 0.010 and about 0.050 inches long and between about 0.002 and about 0.010 inches wide.

7. The valve of claim 1 wherein the shape of said aperture is round.

8. The valve of claim 7 wherein the diameter of said round aperture is between about 0.005 and about 0.010 inches.

9. The valve of claim 1 further including a spring loaded quick release valve for rapid depressurization.

10. An automatic air pressure deflation regulator for use in a sphygmomanometer, said regulator comprising a housing having an air flow channel extending through the longitudinal extent thereof, at least one air deflation port and at least one pressure release port, each of said ports extending outwardly from said channel;

said at least one air deflation port including a floatably mounted deformable diaphragm of substantially uniform thickness supported only on its outer edges by a pair of O-rings on either side of said diaphragm and having an aperture extending through the thickness thereof, wherein said diaphragm is adapted to axially deform along its entire longitudinal extent according to the air pressure applied against it from said channel in order to change the size and shape of said aperture as a function of the air pressure applied against it from said channel to produce a constant air deflation rate therethrough; and wherein said at least one pressure release port includes a quick-release valve for rapid depressurization, said valve including a spring restrained plunger adapted to seal against an O-ring in an un-activated state.

11. An automatic air pressure deflation regulator for use in a sphygmomanometer, said regulator comprising a housing having an air flow channel extending through the longitudinal extent thereof and at least one air deflation port including a floatably mounted deformable diaphragm of substantially uniform thickness supported only on its outer edges and having a center aperture extending through the thickness thereof, said diaphragm further including a stiffening layer on one surface thereof extending inwardly from the outer edge of said diaphragm toward said diaphragm and defining an unstiffened center area surrounding said center aperture, said unstiffened center area being adapted to deform according to the air pressure applied against it from said channel in order to change the size and shape of said aperture as a function of the air pressure applied against it from said channel to produce a contant air deflation rate therethrough.

12. The regulator of claim 11 wherein said regulator further includes at least one pressure release port extending outwardly from said channel.

13. The regulator of claim 12 wherein said pressure release part includes a quick release valve for rapid depressurization, said valve including a spring restrained plunger adapted to seal against an O-ring in an unactivated state.

* * * * *